United States Patent
Cornacchia, III

(10) Patent No.: US 7,725,479 B2
(45) Date of Patent: May 25, 2010

(54) UNIQUE PERSON REGISTRY

(76) Inventor: Louis G. Cornacchia, III, 110 Ocean Blvd., Point Lookout, NY (US) 11569

( * ) Notice: Subject to any disclaimer, the term of this patent is extended or adjusted under 35 U.S.C. 154(b) by 442 days.

(21) Appl. No.: 11/498,951

(22) Filed: Aug. 3, 2006

(65) Prior Publication Data

US 2007/0033174 A1 Feb. 8, 2007

Related U.S. Application Data

(63) Continuation-in-part of application No. 11/083,865, filed on Mar. 18, 2005.

(51) Int. Cl.
*G06F 17/30* (2006.01)
(52) U.S. Cl. .......................... 707/758; 707/781; 705/2; 705/3
(58) Field of Classification Search ........................ None
See application file for complete search history.

(56) References Cited

U.S. PATENT DOCUMENTS 7,318,059 B2 * 1/2008 Thomas et al. ................. 707/3
2001/0041991 A1 * 11/2001 Segal et al. ..................... 705/3
2002/0143580 A1 * 10/2002 Bristol et al. .................. 705/2

* cited by examiner

*Primary Examiner*—John E Breene
*Assistant Examiner*—Thu-Nguyet Le
(74) *Attorney, Agent, or Firm*—Hayes Soloway P.C.

(57) ABSTRACT

A computer-based method is provided for registering a person in a person registry. The method includes: if a unique person identifier is not received, searching an address book for a match to the person using a search criteria input by a user; and if no match to the person is found, receiving person data input by a user and determining whether the person data satisfies a minimum data requirement, wherein the person data is representative of the person, if it is determined that the minimum data requirement is satisfied, determining whether there is a shared entity that represents the person, and if it is determined that no shared entity represents the person, based on an outcome of a non-shared entity-shared entity reconciliation, either defining a shared entity to represent the person in the address book, transforming a non-shared entity into a shared entity, or transferring data from a non-shared entity to a shared entity.

30 Claims, 10 Drawing Sheets

Results found:

| Name | Birthdate | Address | Phone | Email | Eye Color |
|---|---|---|---|---|---|
| Jane Doe | 11/11/1911 | 1 Main Street, Rockville Centre, NY, 11570 | 5165553212 | doctations@doctations.com | Blue |

Top 1 out of 1 total results.

[ Refine Search ]

FIG. 7

Patient Demographic Information

| Field | Value | Ref |
|---|---|---|
| Last Name* | Doe | 631 |
| First Name* | Jane | 632 |
| Middle Name | | 633 |
| Address Line 1* | 1 Main Street | 811 |
| Address Line 2 | | 812 |
| Country* | USA | 813 |
| State/Region* | NY | 814 |
| City/Town* | Rockville Centre | 815 |
| Postal Code* | 11570 | 816 |
| Phone Number (no hyphens or spaces)* | 5165553212 | 820 |
| Email Address (e.g. abcdef.com) | doctations@doctations.com | 825 |
| Social Security Number (no hyphens or spaces) | 999999999 | 637a |
| Government ID | | 637b |
| Date of Birth (mm/dd/yyyy)* | 11/11/1911 12:00:00 AM | 634 |
| Sex* | F | 833 |
| Marital Status* | Single | 835 |
| Eye Color* | Blue | 636 |
| Birthplace | New York City, NY | 635 |
| *required field | No User Name For this Person | 841 |

[Submit] — 850

Additional Patient Information

| Field | Ref |
|---|---|
| Emergency Contact Name: | 911 |
| Emergency Contact Phone Number: | 913 |
| Emergency Contact Relationship: | 915 |
| Pharmacy Name: | 922 |
| Pharmacy Phone Number: | 926 |
| Primary Care Doctations ID: | 931 |
| Primary Care Name: | 933 |
| Primary Care Address: | 935 |
| Primary Care City State Zip: | 937 |
| Primary Care Phone Number: | 939 |
| Referring Doctations ID: | 941 |
| Referring Name: | 943 |
| Referring Address: | 945 |
| Referring City State Zip: | 947 |
| Referring Phone Number: | 949 |
| Employer Name: | 951 |
| Employer Address: | 953 |
| Employer City State Zip: | 955 |
| Employer Phone Number: | 957 |
| Occupation: | 959 |
| Primary Insurer: | 962 |
| Primary Ins ID: | 964 |
| Primary Ins Group: | 966 |
| Primary Ins Phone Number: | 968 |
| Secondary Insurer: | 971 |
| Secondary Ins ID: | 973 |
| Secondary Ins Group: | 975 |
| Secondary Ins Phone Number: | 977 |

Submit — 950

FIG. 9

UNIQUE PERSON REGISTRY

CROSS-REFERENCE TO RELATED PATENT APPLICATION

This is a Continuation-In-Part Application of U.S. application Ser. No. 11/083,865, filed Mar. 18, 2005 and entitled "SYSTEM AND METHOD FOR REMOTELY INPUTTING AND RETRIEVING RECORDS AND GENERATING REPORTS," the content of which is herein incorporated by reference in its entirety.

BACKGROUND OF THE INVENTION

1. Technical Field

The present disclosure relates to secure databases and, more particularly, to methods and systems for defining a person in a shared database as a unique entity.

2. Discussion of Related Art

It has been the practice of professionals, such as doctors, lawyers, and engineers to personally record pertinent information on a subject patient, client or matter so that professional services performed and data pertinent to the subject are documented. The documented information can be in many different forms, such as a patient record database with patient demographic information and clinical data, an engineer's report on the structural conditions of a building, or an invoice including professional fees, travel and other expenses related to the services performed.

In many instances, the professional memorializes the pertinent data or basis for a decision contemporaneously as services are performed, such as by handwritten notes or dictation into a voice recorder, and the information is subsequently gathered for office personnel to enter into a report. Many reports are standardized as forms and the gathered information is filled into the form for efficient reporting. For example, in the case of a physician examining a patient, clinical information is developed during discussions with and physical examination of the patient. The physician dictates or writes the clinical information observed during the examination, and the forms and notes are typically entered by the physician's office personnel. Likewise, the structural engineer dictates or writes his observations during a visual inspection, and a building inspection report is generated by filling in a form-like report with standard pre-filled text on general building condition, supplemented by contemporaneous information using the recorded dictation.

In the case of patient information and report, a patient is typically required to complete a questionnaire which discloses personal information about the patient including medical background information such as pre-existing medical conditions and prescription medications. The reliance on patients to keep track of and report their medical histories, however, can leave the attending medical professional with incomplete and sometimes inaccurate information. For example, patients lose records and may not remember when they had their tonsils out or what vaccinations they received, and their medical records can be damaged or destroyed, e.g., when Hurricane Katrina happens. The patient questionnaire may also establish a patient's current medical condition. A patient history file is opened and the completed questionnaire and other documents are incorporated into the file.

When a patient is examined by a physician, the results of the physical examination or clinical information are routinely recorded such as by the physician entering the information onto a form which is then placed in the patient's history file. It is common practice for the physician to make handwritten notes during the patient's physical examination. The notes are later used by the healthcare professional for personally dictating a patient's report. The dictation is then transcribed, reviewed and signed by the physician who conducted the patient's physical examination.

In the case of medical offices operating under health maintenance organization (HMO) oversight, requiring audits of the examination notes of medical professionals for consistency and trends in diagnosis and treatment, the lack of computerized databases for monitoring and updating clinical examination data and the time consuming process of re-transcribing and editing paper charts complicates this auditing process.

For many healthcare organizations, some with file rooms of paper, medical records about their view of a patient's medical history are based on what the patient has told them and any clinical visits or procedures done at that office. These healthcare organizations are akin to silos in the sense that the information that a hospital has about a patient, e.g., in an emergency room visit the patient experienced an allergic reaction to penicillin, the primary care physician may never get that information unless the patient tells the physician about it.

The technology to assemble and store patient records in computer databases as electronic medical records exists and is being deployed in some hospitals and physician offices. Some healthcare providers and insurance companies are forming regional information networks to share electronic medical records as a means to reduce paperwork, minimize costs of billing, and to fight against false claims.

The Standards for Privacy of Individually Identifiable Health Information ("Privacy Rule") limits the circumstances in which an individual's protected health information may be used or disclosed. The Privacy Rule, which was published in final form on Aug. 14, 2002, establishes, for the first time, a set of national standards for the protection of certain health information. The U.S. Department of Health and Human Services issued the Privacy Rule to implement the requirement of the Health Insurance Portability and Accountability Act of 1996 (HIPAA).

A major purpose of the Privacy Rule is to define and limit the circumstances in which an individual's protected health information may be used or disclosed. The Privacy Rule requires that health plans, healthcare clearinghouses, and every healthcare provider, regardless of size, who electronically transmits health information maintain reasonable and appropriate administrative, technical and physical safeguards to ensure the integrity and confidentiality of the information, protect against any reasonably anticipated threats or hazards to the security or integrity of the information, and protect against unauthorized uses or disclosures of the information.

A need exists for a method and system for assembling medical records from disparate computer-based person records and to make them accessible over the Internet such that the electronic medical records are private and secure. A need exists for a method and system for defining a person in a shared database as a unique entity, for example, to ensure the integrity of the information in the shared database. A need also exists for a method and system for defining a patient in a shared database as a unique entity in order to comply with HIPAA requirements to ensure confidentiality of the health information.

SUMMARY OF THE INVENTION

According to an exemplary embodiment of the present invention, a computer-based method is provided for registering a person in a person registry. The method includes: if a unique person identifier is not received, searching an address book for a match to the person using a search criteria input by a user; and if no match to the person is found, receiving person data input by a user and determining whether the person data satisfies a minimum data requirement, wherein the person data is representative of the person, if it is determined that the minimum data requirement is satisfied, determining whether there is a shared entity that represents the person, and if it is determined that no shared entity represents the person, based on an outcome of a non-shared entity-shared entity reconciliation, either defining a shared entity to represent the person in the address book, transforming a non-shared entity into a shared entity, or transferring data from a non-shared entity to a shared entity.

According to an exemplary embodiment of the present invention, a system for defining a patient in a shared database as a unique entity to comply with HIPAA requirements to ensure confidentiality of the health information is provided. The system includes: a first database including an address book and at least one of patient identifying information or demographic information; a second database including clinical data; an instructable data processor for communicating with the first and second databases; an application service in data communication with the instructable data processor; and at least one Internet access device in data communication with the instructable data processor; wherein the application service searches an address book for a match to the person using a search criteria input by a user and if no match to the person is found, receives person data input by the user and determines whether the person data satisfies a minimum data requirement, wherein the person data is representative of the person, and if it is determined that the minimum data requirement is satisfied, determines whether there is a shared entity that represents the person, and if it is determined that no shared entity represents the person, based on an outcome of a non-shared entity-shared entity reconciliation, either defines a shared entity to represent the person in the address book, transforms a non-shared entity into a shared entity, or transfers data from a non-shared entity to a shared entity.

According to an exemplary embodiment of the present invention, a method is provided for generating a unique user account identifier. The method includes: building a string of alphanumeric characters based on a set of data input by a user; randomly encrypting each alphanumeric character in the string according to its position in relation to a random key; searching a database for an exact match to the encrypted string; and if no exact match is found, generating a unique user account identifier based on the encrypted string.

The present invention will become more apparent to those of ordinary skill in the art when descriptions of exemplary embodiments thereof are read with reference to the accompanying drawings.

BRIEF DESCRIPTION OF THE DRAWINGS

FIG. 7 shows the results found page that provides the results for the search criteria entered in the search person page of FIG. 6, according to an exemplary embodiment of the present invention.

FIG. 8 shows the person demographic page that allows the user to validate the person's demographic information, according to an exemplary embodiment of the present invention.

FIG. 9 shows the additional person information page that allows the user to input emergency contact, primary care doctor, pharmacy information, referring doctor, employer and insurance information, according to an exemplary embodiment of the present invention.

DESCRIPTION OF EXEMPLARY EMBODIMENTS

Figure 1:
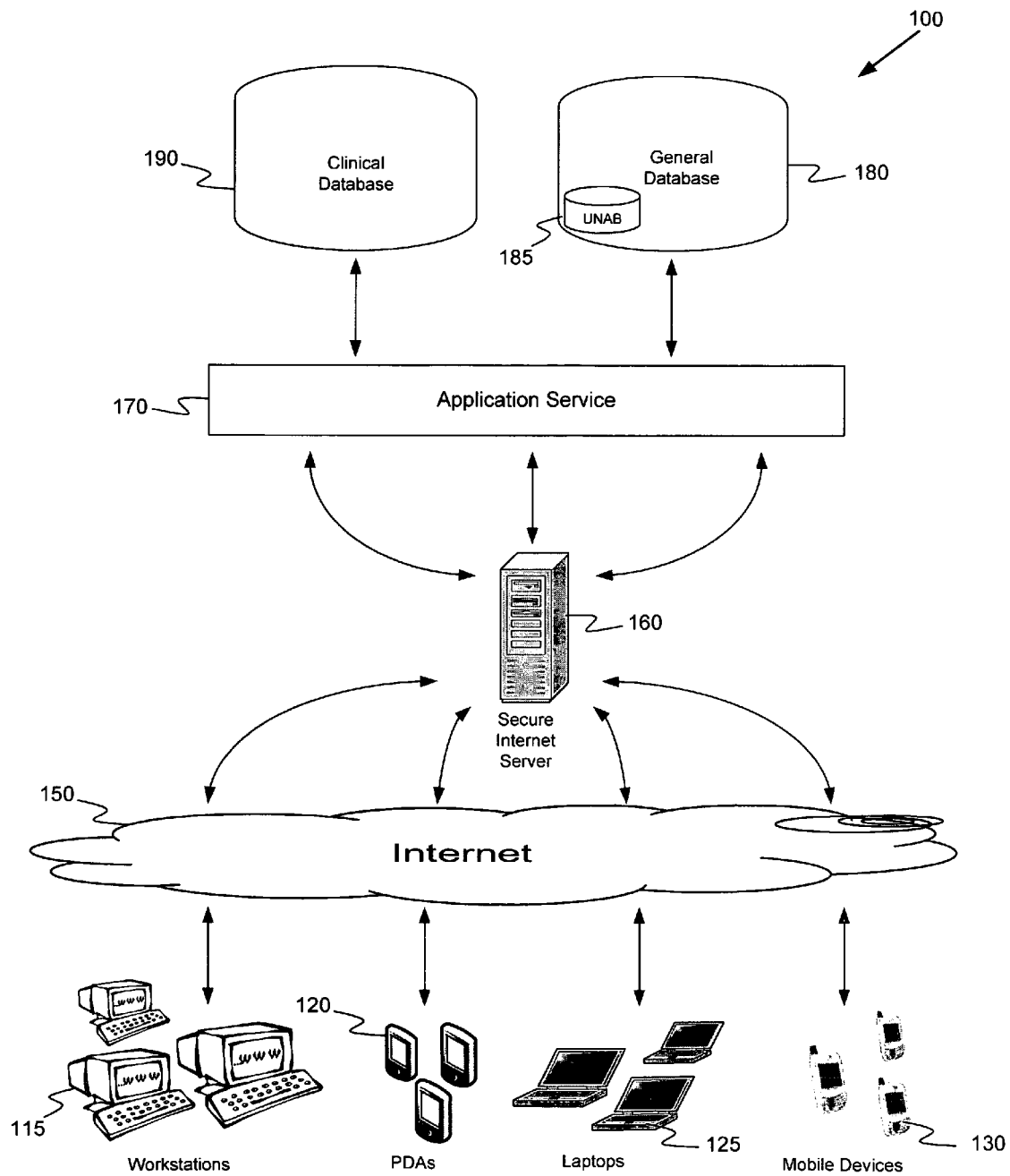
FIG. 1 illustrates a computer network suitable for use in accordance with an exemplary embodiment of the present invention.

Hereinafter, exemplary embodiments of the present invention will be described in detail with reference to the accompanying drawings. Like reference numerals refer to similar of identical elements throughout the description of the figures.

As used herein, "healthcare organizations" refers to the various registered business entities for healthcare from solo practices to surgical centers and hospitals. Examples of healthcare organizations include New York Neurosurgery & Neuroscience Associates (NYNNA), Mercy Medical Center, and Syosset Hospital. As used herein, "Doctations UniqueID" refers to an exemplary system-supplied unique user account identifier, and "iBeWell user account" refers to an exemplary person-selected unique user account identifier.

FIG. 1 illustrates a computer network suitable for use in accordance with an exemplary embodiment of the present invention. It should be understood that the elements shown in FIG. 1 may be implemented in various forms of hardware, software or combinations thereof.

Referring to FIG. 1, a computer network 100 includes clinical database 190, general database 180, application service 170, secure Internet server 160, and at least one Internet access device, such as for example, workstation 115, PDA 120, laptop (or notebook) computer 125, or other Microsoft Windows-enabled mobile devices 130. The computer network 100 also includes a software subsystem called the "universal address book", which maintains information on all entities in the system. In an exemplary embodiment of the present invention, a universal address book (UNAB) datastore 185 is contained in the general database 180.

The information such as person identifying and demographic information stored in the general database 180 may be separated from the data that is stored in the clinical database 190. The general database 180 is designed to be run either integrated with the other database tables or hosted as a separate database system in a geographically different site from the clinical database 190. When hosted separately, a hacker who succeeds at hacking into one site will not obtain the other's information. For example, if a hacker were to hack into the clinical database 190 the hacker would not have the person identifying information. To increase security and privacy, the demographic data and/or clinical data may be encrypted. The connection between the UNAB datastore 185 and the clinical database 190 may also be encrypted.

The secure Internet server 160 includes modules to facilitate access to/from application service 170 to the various Internet access devices 115, 120, 125 and 130 connected to the network over the Internet 150. The workstations 115, for example, may be a fixed or portable personal computer equipped with a computer monitor or screen, a keyboard, a microphone and/or a camera, software modules for browsing hypertext or hypermedia pages, a set of computer speakers and a computer mouse.

Secure Internet server 160 may include an instructable data processor which can be coupled to a hard disk, a keyboard, mouse, and/or another form of user interface (e.g., microphone) as well as to a video card and display device, a network interface card, telephony cards and circuits, and random access memory (RAM), where the latter alone or in combination with the hard disk may contain system software which provides instruction signals for instructing the data processor and/or other instructable data processor to carry out machine-implemented operations in accordance with the present disclosure.

Generally, data or information can be input into the secure Internet server 160 from the various Internet access devices 115, 120, 125 and 130 over the Internet 150 without software specially made for the secure Internet server 160. Specific software that may be needed from time to time can be downloaded from the secure Internet server 160 and installed at the various Internet access devices 115, 120, 125 and 130. For example, security software for user identification or authentication can be loaded at the user's station and used to ensure the user is a registered subscriber. Commercially available software such as VoiceID or Pronexus VBVoice can be used for the speaker identification process.

The UNAB may include a person registry. The UNAB may also include a physician's address book (PAB) (also referred to herein as a "healthcare organization's address book"). The UNAB includes person entities which may be broadly categorized into types. In an exemplary embodiment of the present invention, the UNAB includes non-shared entities and shared entities, and all person entities are flagged as one type or the other. Identifying all person entities as either a shared entity or a non-shared entity may be useful in order to comply with HIPAA requirements to ensure confidentiality of the health information. The UNAB may also include various other types of entities such as business entities.

The PAB or the healthcare organization's address book extracts from the UNAB datastore 185 for those entities that are defined in the PAB. The PAB comprises a combination of non-shared entities and shared entities. The PAB includes a list of physicians in that healthcare organization. The PAB may also include a list of business and other service providers used by that healthcare organization. In an exemplary embodiment of the present invention, the PAB provides a healthcare organization a complete address book of every person in their service.

A person may be registered as a non-shared entity or a shared entity. Hereinafter, the meaning of the terms "non-shared entity" and "shared entity" will be described.

The general database 180 includes person entities and business entities. In the case of an individual doing business as a sole proprietorship, he or she would exist as a person entity and could also be a business entity. Person entities may be broken down into multiple roles. Business entities may be broken down by type.

There are individual attributes about a person, e.g., birthplace, date of birth and eye color, that are related to the person no matter what role the person currently works in. In the general database 180, a person could be a entity, e.g., in the role of a patient or that of a healthcare legal adviser, or a business entity, e.g., Jane Doe LLC.

In the general database 180, there may be a single entry for the person Jane Doe, which may be further defined or redefined based upon a particular role at a particular time in a particular situation. In accordance with an exemplary embodiment of the present invention, a person's privileges tie into whatever role s/he is currently assuming. For example, when Jane Doe goes to her primary care physician, she has a certain birth date, eye color, and other personal attributes, but she takes on the role of a patient in that situation. When Jane Doe is talking with other persons in her role as, for example, a healthcare legal adviser, she still has the same birth date, eye color, etc., but she is allowed to do very different things in this different role. For example, based on what Jane Doe is going to do with the service application 170, she assumes a certain role and is given the rights and privileges of the role.

In an exemplary embodiment of the present invention, every person entity contained in the UNAB is identified as a non-shared entity or a shared entity. A non-shared entity may be distinguished from a shared entity based on the completeness of the information about that person in the general database 180. In an exemplary embodiment of the present invention, there is a certain minimum set of data that is required, and a full complement that is recommended. For example, a shared entity will have the full complement of information defined for that person. A non-shared entity will have some subset of that full complement. When the full complement of information is provided, it allows the service application 170 to determine the individual as a unique person in the general database 180.

The completeness of the information about an individual allows the service application 170 to do the unique identification. For example, when the service application 170 can identify Jane Doe uniquely, she becomes a shared entity in the general database 180—and healthcare organizations in the system and to which Jane Doe granted authorization can access Jane Doe's shared health information. In the case when the service application 170 can not determine a person's uniqueness, e.g., because the full complement of information was not entered, the person may be added as a non-shared entity when registered by some healthcare organization. In cases where it may be possible to determine a person's uniqueness without the full complement of data—for example, a person does not want to provide date of birth or some other information, but even without that information they are nevertheless unique—the person will be added only as a non-shared entity. The reason for adding the person as a non-shared entity, under such circumstances, is that the "next" Jane Doe could come along and she could provide her date of birth, but it would not be possible to distinguish her from the "first" Jane Doe who didn't give her birth date. For example, the next Jane Doe could actually be the first Jane Doe who decided now to provide her date of birth. Although it may be possible, at least in theory, to determine uniqueness from fewer fields, conflicts could arise in the future. As will be described later in this disclosure, there is a minimum data requirement that must be satisfied. When that certain minimum set of information is not provided, according to an exemplary embodiment of the present invention, the person is added as a non-shared entity. Methods of registering a person in a person registry according to exemplary embodiments of the present invention will be described hereinafter with reference to FIGS. 1, 2, 3, 4 and 6 through 10.

Figure 2:
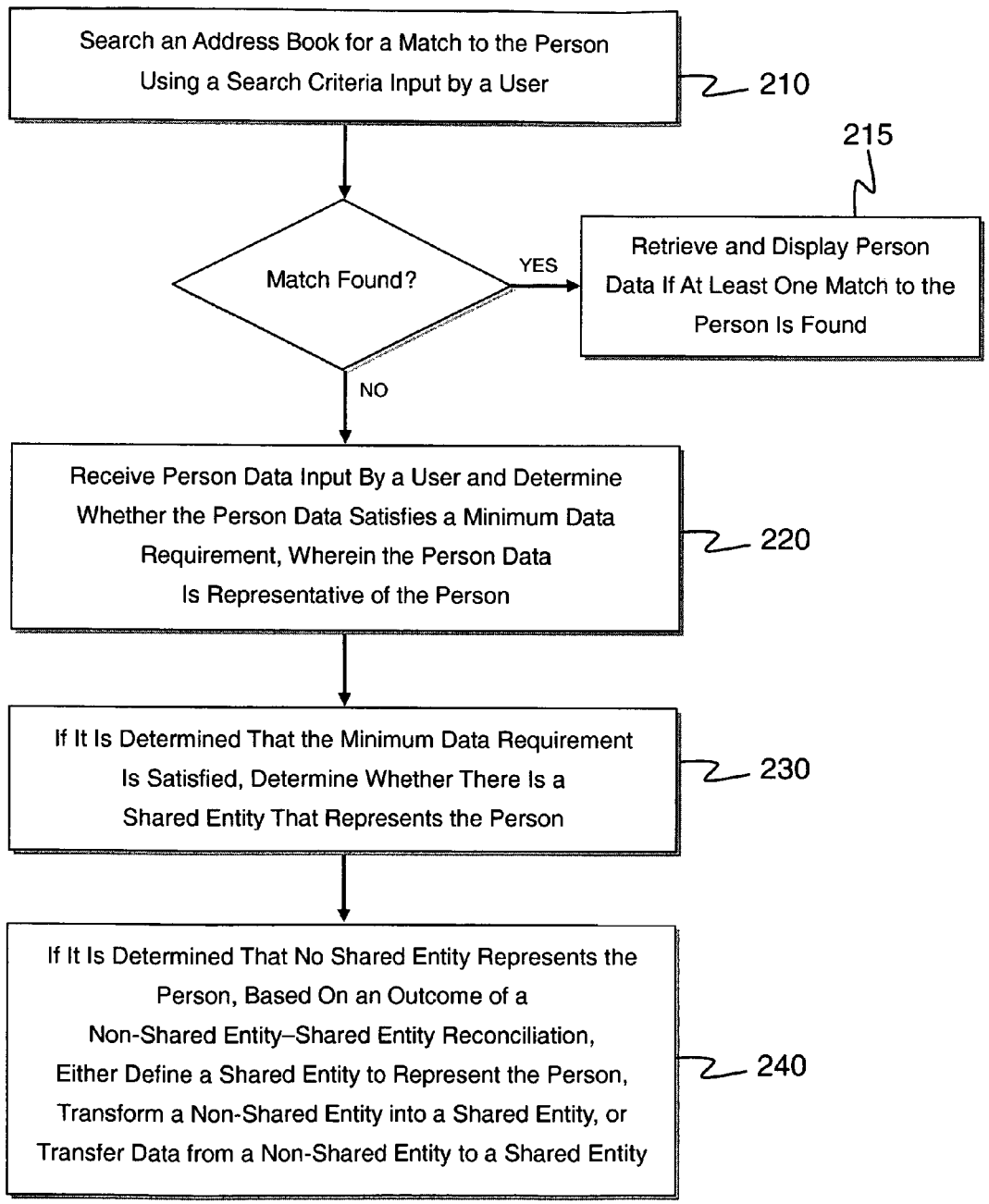
FIG. 2 is a flowchart showing a method of registering a person in a person registry, according to an exemplary embodiment of the present invention.

FIG. 2 is a flowchart showing a method of registering a person in a person registry, according to an exemplary embodiment of the present invention. Referring to FIG. 2, in a step 210, search an address book for a match to the person using a search criteria input by a user. For example, the address book may be the UNAB. The search criteria may comprise person identifying information and/or demographic information input by the user.

In an exemplary embodiment of the present invention, searching the address book for a match to the person comprises searching the address book for a match to the person if a unique person identifier is not received. The unique person identifier may comprise, for example, a system-supplied unique user account identifier and/or a person-selected unique user account identifier.

In a step 215, if at least one match to the person is found, retrieve and display person data. The step 215 may include setting a first flag to indicate either a shared entity or a non-shared entity.

Figure 3:
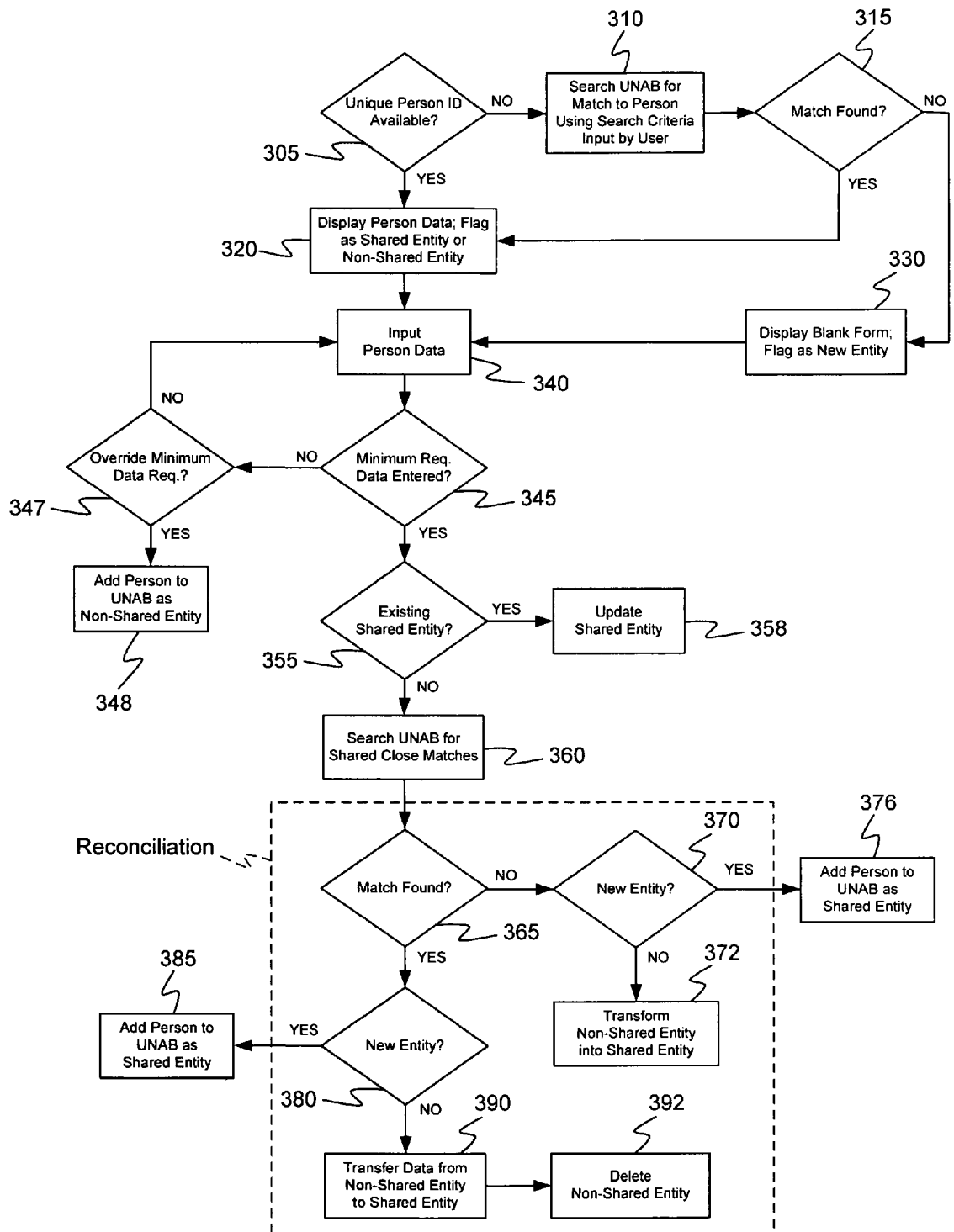
FIG. 3 is a flowchart showing a method of registering a person in a person registry, according to an exemplary embodiment of the present invention.

If no match to the person is found, then, in a step 220, receive person data input by a user and determine whether the person data satisfies a minimum data requirement, wherein the person data is representative of the person. In a step 230, if it is determined that the minimum data requirement is satisfied, determining whether there is a shared entity that represents the person. In a step 240, if it is determined that no shared entity represents the person, based on an outcome of a non-shared entity-shared entity reconciliation, either defining a shared entity to represent the person in the address book, transforming a non-shared entity into a shared entity, or transferring data from a non-shared entity to a shared entity Search by Id FIG. 3 is a flowchart showing a method of registering a person in a person registry, according to an exemplary embodiment of the present invention. In an exemplary scenario, a person visits a doctor and fills out a questionnaire, entirely or in part. When the front desk person begins to register the patient into the healthcare organization's address book, the first question may be whether the person has a Doctations UniqueID (an exemplary system-supplied unique user account identifier) or an iBeWell user account (an exemplary person-selected unique user account identifier). It is to be understood that an iBeWell user account is an example of a person account and that the present invention may be embodied having various person accounts. In the interests of clarity and simplicity, only the Doctations UniqueID and one example of a person account—the iBeWell user account—will be described.

In the case when the person created an account in the patient portal ("iBeWell.com") the person will have an iBeWell user account, or in the case when the person has seen another doctor who uses the service application 170, the person will have a Doctations UniqueID, or the person could have both a Doctations UniqueID and a user account from the patient. As will be described later in this disclosure, if the person has both a Doctations UniqueID and an iBeWell user account, service application 170 can find the person directly because the Doctations UniqueID and iBeWell user account are unique to an individual person and are linked. Those two unique user account identifiers are identifying characteristics for that person in the UNAB. In such case, the front desk person presents a Doctations UniqueID card, the front desk person scans it or otherwise enters the ID information, and service application 170 brings up that person's health information.

The existence of the Doctations UniqueID does not, in and of itself, mean that a person is a shared entity. However, if a person registered in iBeWell and has an iBeWell user account, the person is a shared entity. In an exemplary embodiment of the present invention, obtaining an iBeWell user account requires that the full complement of information is entered.

Search by Person Information

Figure 6:
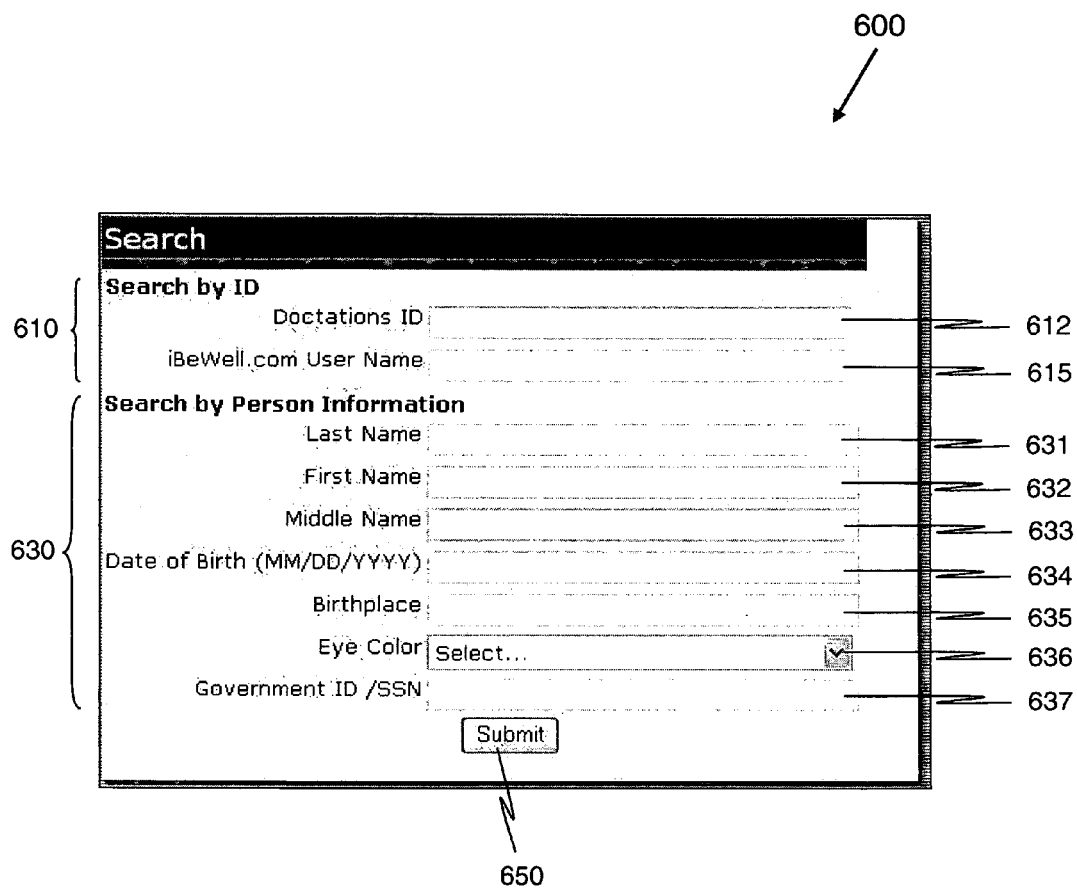
FIG. 6 shows the search person page that allows the user to input search criteria, according to an exemplary embodiment of the present invention.

FIG. 6 shows the search person page that allows the user to input search criteria, according to an exemplary embodiment of the present invention. Referring to FIG. 6, the search person page 600 includes both a search by ID section 610 and a search by person information section 630. It is to be understood that various configurations of the search person page are suitable for implementing the present invention. For example, determining whether the person has a Doctations UniqueID or an iBeWell user account could be determined from the answer to a yes or no type question. If yes, prompt the user to enter a Doctations UniqueID or an iBeWell user account. The search by ID section 610 information could be supplied using a hardware device such as a card scanner to read in the Doctations UniqueID or iBeWell user account information.

Referring to FIG. 3, in a step 305, determine whether a unique person ID is available. For example, the unique person identifier may comprise a system-supplied unique user account identifier (e.g., Doctations UniqueID) and/or a person-selected unique user account identifier (e.g., iBeWell user account). If a unique person ID is available, then in a step 320 display the stored person data. This step may include setting a first flag to indicate whether that person is a shared entity or non-shared entity.

If a unique person ID is not available—e.g., the person does not have a Doctations UniqueID or an iBeWell user account—search the UNAB for a match to the person using search criteria input by a user in a step 310. The search criteria may include, for example, person identifying information and/or demographic information.

In an exemplary embodiment of the present invention, person identifying information includes last name, first name, middle name, date of birth, place of birth, eye color, a government identification and/or social security number. Person demographic information may include, for example, last name, first name, middle name, address, country, state/region, city/town, postal code, phone number, e-mail address, social security number, government ID, age, date of birth, sex, marital status, eye color, birthplace, and/or username.

In an exemplary embodiment of the present invention, person identifying information includes last name, first name, middle name, mother's maiden name, sex at birth (e.g., male, female, other), if female and married, maiden name, result of multiple birth (e.g., yes, no, do not know), identical sibling (e.g., yes, no, do not know), birth order (e.g., 1-50, do not know), date of birth, city of birth, state/region of birth, country of birth, eye color, blood type (e.g., blood type, do not know), race (e.g., Native American or Eskimo=1, Hispanic or Latino=2, Black or African American=3, White/Caucasian (non-Hispanic)=4, Asian or Pacific Islander=5, Other=6, do not know), left hand span (e.g., inches or centimeters), head circumference (e.g., inches or centimeters), father's first name, nearest aged sibling's first name, and dominant writing hand.

In a step 330, display a blank form if no match to the person is found in the UNAB. This step may include setting a second flag to indicate a new person. In this case, the person registration starts from zero—and a certain minimum set of person data is required to be entered. In an exemplary embodiment of the present invention, the minimum set of person data that is required is last name, first name, middle name, date of birth, birthplace, eye color, and government ID/social security number (SSN). In an exemplary embodiment of the present invention, the minimum set of person data that is required is last name, first name, middle name, mother's maiden name, sex at birth, maiden name, result of multiple birth, identical sibling, birth order if result of multiple birth, date of birth, city of birth, state/region of birth, country of birth, eye color, blood type, race, left hand span, head circumference, father's first name, nearest aged sibling's first name, dominant writing hand, and e-mail address. Optional data may include driver's license number, government ID, social security number, nearest sibling's first name, and maiden name. The person data is input by a user in a step 340, as shown in FIG. 3.

Referring to FIG. 6, the search by person information section 630 of the search person page 600 includes data entry fields for last name 631, first name 632, middle name 633, date of birth 634, birthplace 635, eye color 636, and government ID/SSN 637. It is to be understood that the search person page 600 may be embodied in various configurations. For example, the data entry fields may include last name, first name, middle name, mother's maiden name, sex at birth, maiden name, result of multiple birth, identical sibling, birth order if result of multiple birth, date of birth, city of birth, state/region of birth, country of birth, eye color, blood type, race, left hand span, head circumference, father's first name, nearest aged sibling's first name, dominant writing hand, and e-mail address, driver's license number, government ID, social security number, nearest sibling's first name and/or maiden name if married and female.

When the data is entered, the user clicks the submit button 650 to submit the supplied data. As shown in FIG. 3, in a step 345, determine whether the required data is entered such that a minimum data requirement is satisfied. For example, determining whether the minimum data requirement is satisfied may comprise validating the data entry against a requirement.

If the required data is entered, then, in a step 355, determine whether the person is a shared entity (e.g., whether a shared entity represents the person in the UNAB). For example, this determination may comprise checking whether a first flag (e.g., a flag set in step 320) indicates a shared or non-shared entity. If the flag indicates that the person is a shared entity, then, in a step 358, the clinical database 190 is updated with the shared person's new health information. After the clinical database 190 is updated, healthcare organizations in the system and to which the person granted authorization (e.g., person signed a form authorizing access to the information) will then have access to that new health information.

If a person is a shared entity and has authorized a certain healthcare organization to access the person's medical records, then instead of the doctor at that healthcare organization looking at their own database of paper records, online data, etc., the doctor looks in the clinical database 190. All the healthcare organizations that the person has authorized are able to look into the clinical database 190. For example, when the record of that emergency room visit is updated to the clinical database 190, every doctor automatically the next time they look at the person's health record can see that information. That information is available from setting to setting whenever the person is referred, transferred, or otherwise seen by another healthcare provider.

When the person is a shared entity in the system, the person is no longer the lone information conduit between healthcare organizations, and the information about the person from a health perspective at each individual healthcare organization gets broader. For example, allowing the healthcare provider a broader knowledge of a person's health record is important for diagnosis and person care with the goal of improving treatment outcomes.

Emergency Situation Override

Referring to FIG. 3, if the minimum required data is not entered, then, in a step 347, determine whether to override the minimum data entry requirement, for example, based on user input. If yes, e.g., an emergency situation, then add the person to the UNAB as a non-shared entity in a step 348.

For example, in the case when an individual sustained injuries in an accident and the only information that a hospital emergency room in the system has about the person is the last thing that she said before she passed out, e.g., my name is Jane Doe. The hospital staff needs to be able to register the accident victim into the system to start collecting clinical data on the person. In such a situation, the person is added as a non-shared entity.

Search for Close Matches

A search of the UNAB for shared close matches, in a step 360, may precede a reconciliation process shown by a dashed box in FIG. 3, which will be described later in this disclosure. In this exemplary scenario, no unique person ID is available (e.g., the person does not have a Doctations UniqueID or an iBeWell user account), the minimum required person data has been entered, and it has been determined that the person is not a shared entity. When the person is not a shared person—for example, the person is registering for the first time or a healthcare organization that registered the person did not enter the minimum required person data—a search for close shared entity matches may be performed. In an exemplary embodiment of the present invention, the close match search is based on person identifying information and/or demographic information.

The search for close matches may use the data fields in the search by person information section 630 of the search person page 600 shown in FIG. 6. In an exemplary embodiment of the present invention, the search for close matches may use last name, first name, middle name, mother's maiden name, sex at birth, maiden name, result of multiple birth, identical sibling, birth order, date of birth, city of birth, state/region of birth, country of birth, eye color, blood type, race, left hand span, head circumference, father's first name, nearest aged sibling's first name, and/or dominant writing hand.

Figure 4:
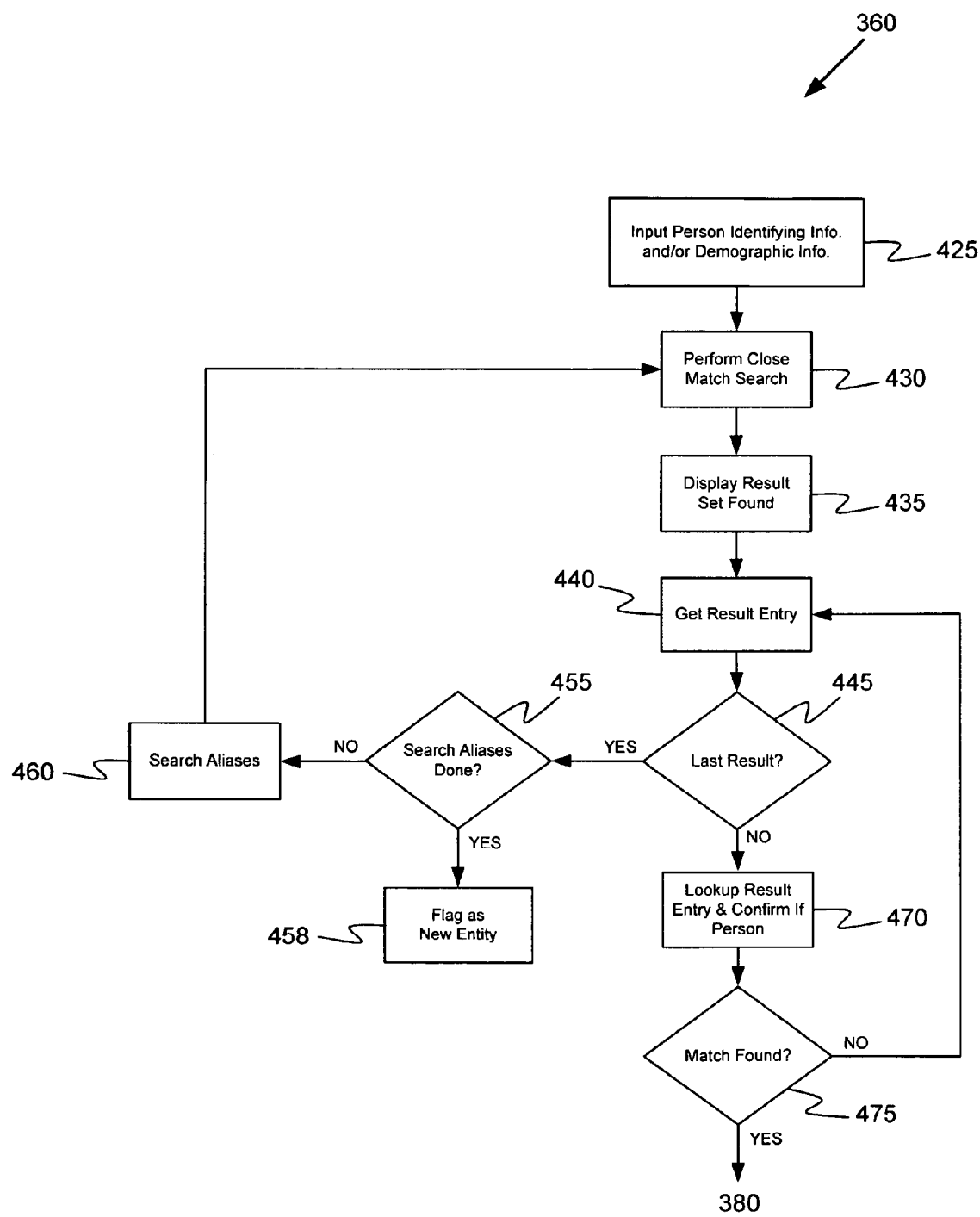
FIG. 4 is a flowchart showing the search for close matches 360 of FIG. 3, according to an exemplary embodiment of the present invention.

FIG. 4 is a flowchart showing a method of searching for close matches, according to an exemplary embodiment of the present invention. Referring to FIG. 4, in a step 425, input the person's identifying information and/or demographic information. For example, the person's last name, first name, middle name, date of birth (DOB), place of birth (POB), eye color, and/or government ID/SSN may be input as the search criteria.

In a step 430, perform a close match search with the search criteria entered in the data fields of the search person page of FIG. 6. At least one of these fields must be entered, entirely or in part, to be searched. For example, a user can enter just a single character S in the last name field, and all entries where the last name starts with S will be returned. Generally, the more data that is specified by the user, the more refined the result set.

In a step 435, display the result set found. The result set will contain all shared entities, because service application 170 looks in the UNAB datastore 185 for shared entities and does not look in healthcare organizations' address books. As results are returned, and the user determines that the result set is too large to use productively, additional data can be specified to reduce the result set to something more manageable.

Suitable methods of searching for close matches may involve one or more of the following three types of search procedures: SOUNDEX search on object name fields (last name, first name, middle name, birthplace); LIKE searches on all fields; and EXACT MATCH searches on all fields. For example, these three searches are combined into one database query and the unique matches are returned. That is, each type of search can return the same object. For example, if the user types in the last name "Smith", all three types of searches could return the same Mary Smith object, as it sounds like the search criteria, contains the search criteria and is an exact match of the search criteria.

SOUNDEX routines are a set of phonetic algorithms for finding similar sounding names, and have become a standard feature in relational database systems for finding data. The algorithm will capitalize all letters and remove punctuation. The first letter is retained; all vowels along with H, W, and Y are removed. Double consonants are converted into a single one. Consonants are assigned a digit (all like sounding consonants are assigned the same digit). Duplicate adjacent digits are removed. The resulting field is padded with 0 to 3 digits max. The SOUNDEX code is created from the retained first letter and the 3 digits.

The search field and the database fields to be searched are SOUNDEXed. Any fields that match the SOUNDEX are returned as "sounds like" matches. For example, searching for Smith will generate a SOUNDEX code of S530. It will match Smithe, Smyth, Smythe, etc., as they also have SOUNDEX codes of S530.

LIKE searches will find all matches of a particular string in database fields, based on wildcard definition. The search can be specified as "starts with", "contains" or "ends with". In an exemplary embodiment of the present invention the search is specified as "starts with". For example, searching for Smith will match anybody with the last name of Smith as well as Smithson, Smithsonian, Smithy, Smithwell, etc.

EXACT MATCH will find exact matches only. For example, searching for Smith will return anybody with the exact last name Smith.

SHARED CLOSE MATCH combines all three types of searches, as described above, and returns unique entries where the person is a shared entity in the UNAB. For example, searching for a close match of Smith will return all Smiths, all Smyths, all Smythes, all Smithsons, all Smithys, etc., where the flag indicates a shared person. It will identify those Smith entities that get returned redundantly because of the match on all three types of search, so that, e.g., Mary Z. Smith will only appear once in the result set.

When multiple fields are used in the search (e.g., when last name and first name are entered, the search will AND these together so that the result set will include those entries that match Smith on the last name AND those entries that match Mary on the first name. This allows the result set to be more refined as more search data is specified.

The situation may occur that, even with a highly specified search, duplicate entries are found. In such case, the result set display will show additional (non-searched) data to aid the user in determining which entry is the unique entry for the person. This additional data may include address, phone number, sex, marital status, etc.

The elimination of duplicates in the system is not guaranteed but ultimately approaches zero. Theoretically it is possible to encounter identical twins, born on the same day in the same location, having the exact same names, living at the same address with the same phone number and marital status, and without an assigned government ID or SSN, but this scenario is improbable to the point of near-impossibility.

FIG. 7 shows the results found page that provides the results for the search criteria entered in the search person page of FIG. 6, according to an exemplary embodiment of the present invention. Referring to FIG. 7, the results found page 700 includes fields for displaying name 730, birth date 634, address 740, phone number 743, e-mail address 745, and eye color 636. Other embodiments of the results found page may include fewer data fields or additional fields. It is to be understood that the results found page 700 may display a single result or multiple results. When there are multiple results, the results found page 700 may display results that contain the minimum set of person data and/or results that do not contain the minimum set (one or more data fields are blank).

In the exemplary scenario illustrated in FIG. 7, the results found page 700 contains the minimum set of person data that is required: Jane Doe, Nov. 11, 1911, 1 Main Street, Rockville Centre, N.Y. 11570, 5165553212, doctatons@doctations.com, Blue. At this point, the front desk person may ask do you live at 1 Main Street, Rockville Centre, and/or what is your social security number—to verify that the results shown in the results found page 700 is a match to the registering person. It is to be understood that the results found page may display more than a single result found, and that the front desk person may ask several questions to ensure that a particular result found actually represents that person's data.

As shown in FIG. 7, the results found page 700 includes a refine search button 755. In an exemplary embodiment of the present invention; a refine search capability is provided.

Referring again to FIG. 4, in a step 440, get result entry. This step will be described in detail with reference to FIGS. 4 and 8.

Person Demographics

FIG. 8 shows the person demographic page that allows the user to validate the person's demographic information, according to an exemplary embodiment of the present invention. Referring to FIG. 8, the person demographic information screen 800 includes fields for person last name 631, first name 632, middle name 633, address line-1 811, address line-2 812, country 813, state/region 814, city/town 815, postal code 816, phone number 820, e-mail address 825, social security number 637a, government ID 63b, date of birth 634, sex 833, marital status 835, eye color 636, birthplace 635, and username 841. When the data is entered, the user clicks the submit button 850 to submit the supplied data.

Referring to FIG. 4, in a step 445, determine whether the last result has been encountered. If the result is the last result in the result set, then, in a step 455, determine whether a search aliases has been done. If a search alias has been done, flag as new entity in a step 458. If a search alias has not been done, then, in a step 460, search on aliases.

If not last result, then, in a step 470, lookup result entry and confirm if it is the person. In step 475, determine whether match found. If no match is found, return to step 440. If a match is found, go to step 380 of FIG. 3.

Non-Shared-Entity—Shared-Entity Reconciliation

When a person is a non-shared entity, s/he is a non-shared entity to at least one healthcare organization, e.g., the person may be in New York Neurosurgery & Neuroscience Associate's PAB (physician's address book). The same person may be a shared entity for Mercy Medical Center. For example, Mercy Medical Center entered the full complement of information, whereas New York Neurosurgery & Neuroscience Associates (NYNNA) doesn't have the full complement because, e.g., the person didn't provide all the information or NYNNA didn't entered it or some other reason. In that situation, when the person goes to NYNNA for which the person is a non-shared entity, they can not access the clinical database 190. NYNAA only knows who the person is in the context of its own non-shared clinical database—so they start working as a silo. Information such as documentation of a clinical encounter at NYNAA can be seen by any of the doctors in the "silo" environment, but information for example regarding the patient's emergency room visit to Syosset Hospital would not be available to NYNNA until the patient tells them.

Referring to FIG. 3, after search for shared close matches step 360, determine whether a match is found in step 365. If no match is found, then, in a step 370, determine whether the person is a new entity. If the person is a new entity, add person to the UNAB as a shared entity in a step 376. If the person is not a new entity—this is the case where a non-shared entity exists for the person and said non-shared entity is determined to be unique—then transform the non-shared entity into a shared entity in a step 372. For example, transforming a non-shared entity into a shared entity may comprise updating the flag set in step 320.

In the case when the search for shared close matches step 360 does yield a match found in step 365, a step 380 is reached. In step 380, determine whether the person is a new entity. If yes update shared entity in the UNAB with the additional data in a step 385. If the person is not a new entity—at this point, meaning that there is both a shared entity and non-shared entity for the person, e.g., the situation where Syosset Hospital did not enter the full complement of information but Mercy Medical Center did so—in such case, the data associated with that non-shared entity is transferred to the shared entity, in a step 390, and the non-shared entity is then deleted. In an exemplary embodiment of the present invention, transferring the data associated with that non-shared entity to the shared entity requires the person's approval.

When the full complement of information is entered, as part of this reconciliation, the person may be notified that, e.g., Syosset Hospital has been operating with a subset of the person's health information, and the person may asked whether s/he wishes to authorize Syosset Hospital to access the shared health information—and this may be done online.

Person Account/Username/Password

In the case when the person created an account in the patient portal the person will have an iBeWell user account. If a person is a shared entity, the person can obtain a username and password to access the system. For example, the person may register for an iBeWell account (a patient account). Hereinafter, system requirements for username and password will be described.

In an exemplary embodiment of the present invention, the username must be unique. In the case when a person wants to access the system, not by, for example, a Doctations UniqueID, but by something that's easy to remember, service application 170 will determine whether the username has already been used.

The password does not have to be unique. However, the password is required to conform to a set of rules that are in place for security purposes. For example, using the password as the username is not allowed. The password may be restricted, for example, to an alphanumeric string of a predetermined minimum length. It is to be understood that industry best practice around what makes a strongly secure password can be built into the password. To handle the situation where the person has forgotten his or her username and/or password, a challenge question may be provided.

Unique Person Identifier

The unique person identifier may comprise a system-supplied unique user account identifier, for example, "Doctations UniqueID" (an exemplary system-supplied unique user account identifier) and/or a person-selected unique user account identifier (e.g., iBeWell user account).

According to an exemplary embodiment of the present invention, a method of generating a unique user account identifier includes building a string of alphanumeric characters based on a set of data input by a user, wherein each alphanumeric character in the string is randomly encrypting according to its position in relation to a random key. The method includes searching a database for an exact match to the encrypted string, and if no exact match is found, generating a unique user account identifier based on the encrypted string.

In an exemplary embodiment of the present invention, a system-supplied unique user account identifier may be based on fields including last name, first name, middle name, mother's maiden name, sex at birth, maiden name, result of multiple birth, identical sibling, birth order, date of birth, city of birth, state/region of birth, country of birth, eye color, blood type, race, left hand span, head circumference, father's first name, nearest aged sibling's first name, and/or dominant writing hand. Each of the fields may be separated by a delimiter (|) and the entire sequence may be randomly encrypted, and equal characters will encrypt to different values at different indexes. For example: XOR encrypted (Rubinstein|Erez|||Male|1|No||09-29-1985|Haifa|Haifa||Israel|Brown|A). The delimited string may be encrypted with an XOR encryption scheme using a random key value. This will randomly encrypt every letter in the string differently according to its position in relation to the random key.

To ensure that the final encrypted string representation does not include unreadable characters, such as backspace or carriage return, the string may be further lengthened by transforming each character into its byte representation and creating a new byte sequence string.

In an exemplary embodiment of the present invention, the string is encrypted into a non-readable string of the same length as the original data plus its delimiters. In this case, the ID will be the same length as its original data, but it will not be visually readable.

In another exemplary embodiment of the present invention, the string is encrypted into a non-readable string, each character is transformed into its equivalent byte representation, and the entire number is compressed into a readable base, such as for example, base 70. In this case, the ID will be longer than the original data, however it will be visually readable.

In an exemplary embodiment of the present invention, substantial uniqueness of the unique user account identifier is accomplished by entry of a minimum of 18 fields, in which case the unique user account identifier is unique with greater than 95% certainty. In an exemplary embodiment of the present invention, the minimum fields for achieving substantial uniqueness of the unique user account identifier are: last name, first name, middle name, mother's maiden name, sex at birth, female maiden name, result of multiple birth, birth order, identical sibling, date of birth, city of birth, eye color, blood type, race, head circumference, left hand span, father's first name, nearest-aged sibling's first name and dominant hand.

As shown below, Table 1 includes fields used for generating a system-supplied unique user account identifier according to exemplary embodiments of the present invention.

TABLE 1

| Field | Must have >=21 | Must have <21 |
|---|---|---|
| Last name* | Yes | Yes |
| First name* | Yes | Yes |
| Middle name | | |
| Mother's maiden name* | | |
| Sex at birth* | Yes | Yes |
| If female and married, your maiden name | | |
| Result of Multiple Birth | Yes | Yes |
| Birth Order | Depends on multiple birth | Depends on multiple birth |
| Identical Sibling | Depends on multiple birth | Depends on multiple birth |
| Date of Birth | Yes | Yes |
| City of Birth | Yes | Yes |
| Region of Birth | | |
| Country of Birth | | |
| Eye Color* | Yes | Yes |
| Blood Type* | | |
| Race | | |
| Left hand Span | | Yes |
| Head Circumference | | Yes |
| Father's First Name | | |
| Nearest aged Sibling's First Name | | |
| Dominant Writing Hand | Yes | Yes |

*= key field

In an exemplary embodiment of the present invention, the user will be asked to enter a preset number of mandatory key fields, (e.g., six key fields) and then reentered to ensure the correctness of the registration process. In this exemplary embodiment of the present invention, the six key fields are eye color, sex at birth, first name, last name, mother's maiden name and blood type.

To decrease the average string length, some fields can be excluded from the final string to be converted. For example, instead of using three fields for place of birth, only one may be included, e.g., if country, region, and city are entered, then only need to include the unique city ID from which region and country can be found. If country and region are entered, only need to include the unique region ID from which the country can be found. If only the country is entered, only the country ID will be used.

In another example, the date of birth may be stripped of its delimiter character ('/') giving it a new length of 8, then compressed to a base number, such as base 255, which will compress it to a three digit (character) number. Application of field exclusion processes can decrease the average string length by about 40%, e.g., from 71 characters to 42 characters.

In an exemplary embodiment of the present invention, the user will only be allowed a maximum of eight empty fields. More than 8 empty fields may result in a registering error.

After verification that the user did not exceed the maximum allowable empty fields, it is determined whether the generated unique user account identifier already exists. For example, a database lookup may be performed to search for an exact match to the generated unique user account identifier. If an exact match is found, this is the same user, and the registration process may be stopped.

If the search does not yield an exact match, a fuzzy lookup may be performed. For example, a phonetic search may be performed which disregards most vowels and returns a highest match percentage. In an exemplary embodiment of the present invention, if the highest match percentage is above a certain threshold, the generated unique user account identifier is deemed similar enough to that of another user, and registration process may be stopped and/or further investigation into the matter may be carried out.

In an exemplary embodiment of the present invention, after two unsuccessful registration attempts, a "Help, I want to get in, but the system won't let me" button appears. If pressed, the application will actively contact system and who will be maintaining these requests and ensuring a correct registration process.

In an exemplary embodiment of the present invention, before any successful registration, the user must complete a survey in which he or she rates every registration field on 1-5 scale; 1 being great, and 5 being offensive. The questionnaire will also contain a section in which the user may provide comments on the general registration process. These statistics may be collected in order to further improve the registration process.

Additional Person Information

FIG. 9 shows the additional person information page that allows the user to input emergency contact, primary care doctor, pharmacy information, referring doctor, employer and insurance information, according to an exemplary embodiment of the present invention. Referring to FIG. 9, the additional person information screen 900 includes fields for emergency contact name 911, emergency contact phone number 913, emergency contact relationship 915, pharmacy name 922, pharmacy phone number 926, primary care Doctations UniqueID 931, primary care name 933, primary care address 935, primary care city state zip 937, primary care phone number 939, referring Doctations UniqueID 941, referring name 943, referring address 945, referring city state zip 947, referring phone number 949, employer name 951, employer address 953, employer city state zip 955, employer phone number 957, occupation 959, primary insurer 962, primary insurer ID 964, primary insurer group 966, primary insurer phone number 968, secondary insurer 971, secondary insurer ID 973, secondary insurer group 975, secondary insurer phone number 977. When the data is entered, the user clicks the submit button 950 to submit the supplied data. If all the information is entered, then service application 170 makes a shared entity for the person.

Figure 10:
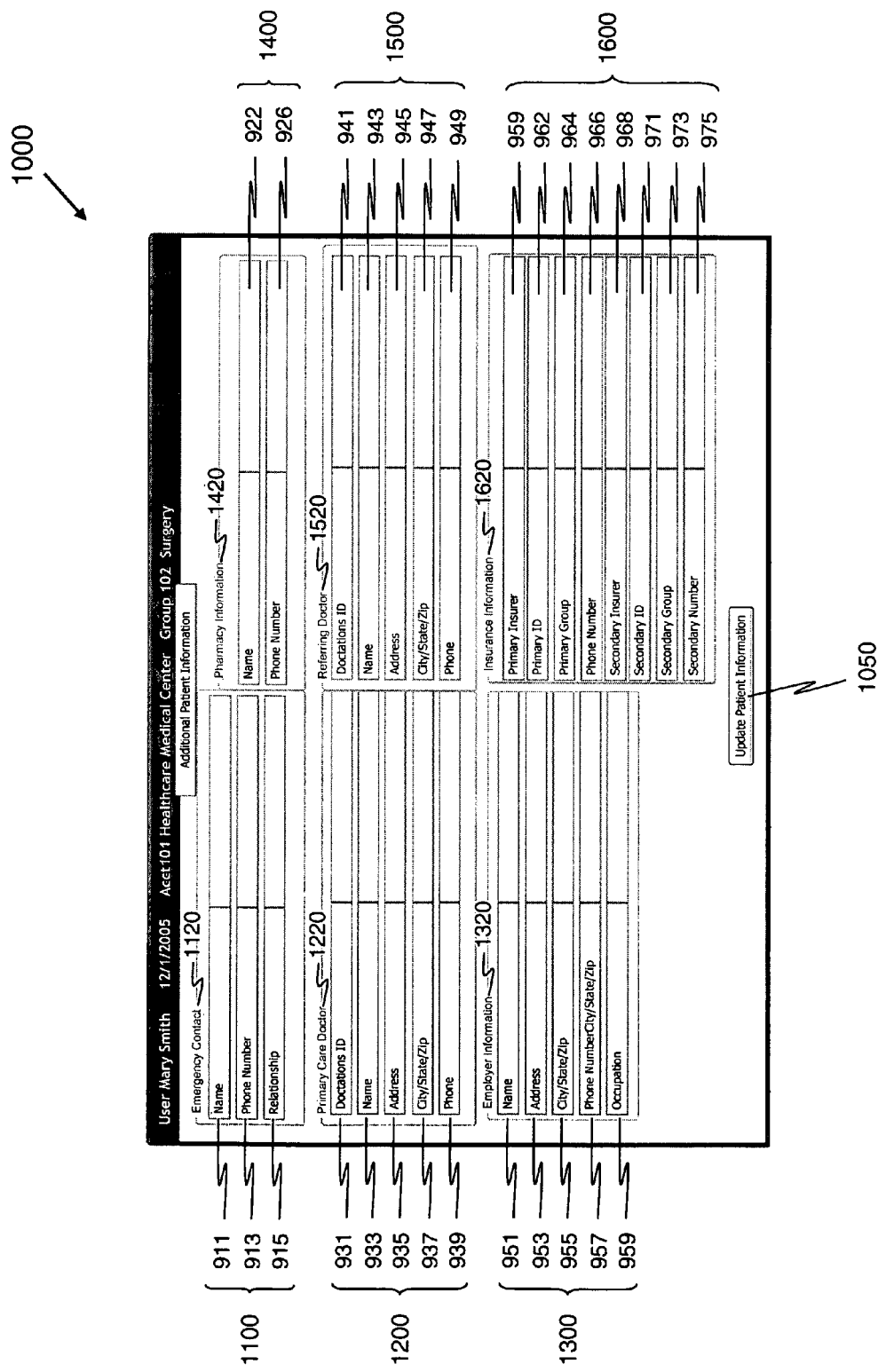
FIG. 10 shows an alternative exemplary embodiment of the additional person information page of FIG. 9.

FIG. 10 shows an alternative exemplary embodiment of the additional person information page of FIG. 9. Referring to FIG. 10, the additional person information screen 1000 includes an emergency contact section 1100, primary care doctor section 1220, employer information section 1320, pharmacy information section 1420, referring doctor section 1520, and insurance section 1620.

The emergency contact section 1100 includes fields for emergency contact name 911, emergency contact phone number 913, and emergency contact relationship 915.

The primary care doctor section 1220 includes fields for primary care Doctations UniqueID 931, primary care name 933, primary care address 935, primary care city state zip 937, and primary care phone number 939.

The employer information section 1320 includes fields for employer name 951, employer address 953, employer city state zip 955, employer phone number 957, and occupation 959.

The pharmacy information section 1420 includes fields for pharmacy name 922, and pharmacy phone number 926.

The referring doctor section 1520 includes fields for referring Doctations UniqueID 941, referring name 943, referring address 945, referring city state zip 947, and referring phone number 949.

The insurance section 1620 includes fields for primary insurer 962, primary insurer ID 964, primary insurer group 966, primary insurer phone number 968, secondary insurer 971, secondary insurer ID 973, secondary insurer group 975, and secondary insurer phone number 977. When the data is entered, the user clicks the submit button 1050 to submit the supplied data.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Hereinafter, a computer readable medium including computer code for registering a person in a person registry as a shared entity or a non-shared entity, in accordance with an exemplary embodiment of the present invention will be described. The computer readable medium comprises: computer code for searching an address book for a match to the person using a search criteria input by a user; computer code for receiving person data input by a user and determining whether the person data satisfies a minimum data requirement, wherein the person data is representative of the person, if no match to the person is found; computer code for determining whether there is a shared entity that represents the person if it is determined that the minimum data requirement is satisfied; and computer code for if it is determined that no shared entity represents the person, based on an outcome of a non-shared entity-shared entity reconciliation, either defining a shared entity to represent the person in the address book, transforming a non-shared entity into a shared entity, or transferring data from a non-shared entity to a shared entity.

Hereinafter, a method of searching a person registry for matches according to an exemplary embodiment of the present invention will be described with reference to FIG. 5.

Figure 5:
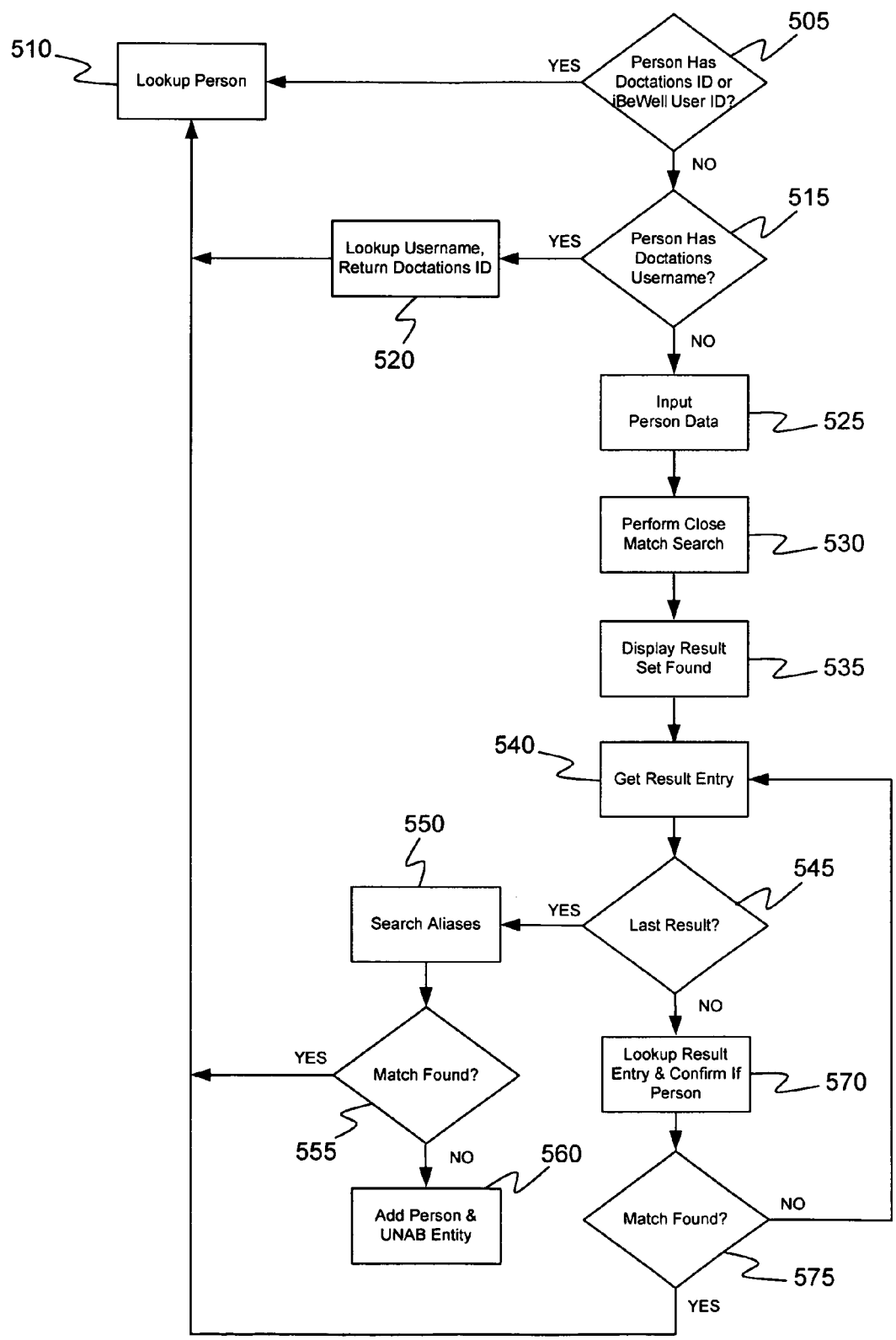
FIG. 5 is a flowchart showing a method of searching a person registry for matches including searching for aliases, according to an exemplary embodiment of the present invention.

FIG. 5 is a flowchart showing a method of searching a person registry for matches, according to an exemplary embodiment of the present invention. Referring to FIG. 5, in a step 505, determine whether the person has a Doctations UniqueID or iBeWell user account. If the person has a Doctations UniqueID and/or iBeWell user account, lookup the person in a step 510. If the person does not have a Doctations UniqueID and/or iBeWell user account, determine whether the person has a Doctations username in a step 515. For example, this is the case when the person has a Doctations UniqueID and/or iBeWell user account but, for whatever reason, provides his or her Doctations username.

If the person has a Doctations username, then, in a step 520, lookup username and return a Doctations UniqueID. Lookup the person with the Doctations UniqueID in the step 510. If the person does not have a Doctations username, then person data input by a user is received in a step 525. For example, person data input by a user may comprise person identifying information and/or demographic information. In an exemplary embodiment of the present invention, the minimum set of person data that is required is last name, first name, middle name, date of birth, birthplace, eye color, and government ID/social security number (SSN).

In a step 530, perform a close match search, for example, with the search criteria entered in the data fields of the search person page of FIG. 6. In a step 535, display the result set found. In a step 540, get result entry.

In a step 545, determine whether the result entry is last result. If not last result, then, lookup the result entry and confirm if person in a step 570. If match found, lookup the person in the step 510. If no match is found, repeat steps 540 and 545.

If the result entry is the last result, then, in a step 550, search aliases. In a step 555, determine whether match found. If no match is found, add person and UNAB entity in a step 560. If a match is found, lookup the person in the step 510.

A system for defining a patient in a shared database as a unique entity to comply with HIPAA requirements to ensure confidentiality of the health information is provided, according to an exemplary embodiment of the present invention, includes: a first database such as general database 180 of FIG. 1 including an address book such as the UNAB, a second database such as the clinical database 190, an instructable data processor for communicating with the first and second databases, an application service 170 in data communication with the instructable data processor, and at least one Internet access device in data communication with the instructable data processor. In an exemplary embodiment of the present invention, the first database is designed to be run either integrated with the second database or hosted as a separate database system in a geographically different site from the second database. Suitable Internet access devices include, for example, workstation 115, PDA 120, laptop (or notebook) computer 125, and/or other Microsoft Windows-enabled mobile devices 130.

The application service 170, according to an exemplary embodiment of the present invention, searches an address book for a match to the person using a search criteria input by a user and if no match to the person is found, receives person data input by the user and determines whether the person data satisfies a minimum data requirement, wherein the person data is representative of the person.

If it is determined that the minimum data requirement is satisfied, the application service 170 determines whether there is a shared entity that represents the person, and if it is determined that no shared entity represents the person, based on an outcome of a non-shared entity-shared entity reconciliation (shown by a dashed box in FIG. 3), either defines a shared entity to represent the person in the address book, transforms a non-shared entity into a shared entity, or transfers data from a non-shared entity to a shared entity. For example, transforming a non-shared entity into a shared entity may comprise updating a first flag.

Although the exemplary embodiments of the present invention have been described in detail with reference to the accompanying drawings for the purpose of illustration, it is to be understood that the inventive processes and systems are not to be construed as limited thereby. It will be readily apparent to those of ordinary skill in the art that various modifications to the foregoing exemplary embodiments can be made therein without departing from the scope of the invention as defined by the appended claims, with equivalents of the claims to be included therein.

What is claimed is:

1. A computer-based method of registering a person in a person registry as a shared entity or a non-shared entity, comprising:
   if a unique person identifier is not received, searching an address book for a match to the person using a search criteria input by a user; and
   if no match to the person is found,
   receiving person data input by a user and determining whether the person data satisfies a minimum data requirement, wherein the person data is representative of the person, if it is determined that the minimum data requirement is not satisfied, generating a non-shared entity to represent the person in the address book, and if it is determined that the minimum data requirement is satisfied, determining whether there is a shared entity that represents the person, and if it is determined that no shared entity represents the person, based on an outcome of a non-shared entity-shared entity reconciliation, performing one of generating a shared entity to represent the person in the address book, transforming a non-shared entity into a shared entity, or transferring data from a non-shared entity to a shared entity, wherein the shared entity grants access to data associated with the shared entity and the non-shared entity prevents access to data associated with the shared entity.

2. The computer-based method of claim 1, wherein the unique person identifier comprises at least one of a system-supplied unique user account identifier or a person-selected unique user account identifier.

3. The computer-based method of claim 2, wherein the system-supplied unique user account identifier is generated in a registration process and wherein a minimum of six key fields entered by the user is used to generate the unique user account identifier.

4. The computer-based method of claim 3, wherein the six key fields are eye color, sex at birth, first name, last name, mother's maiden name and blood type.

5. The computer-based method of claim 4, wherein the system-supplied unique user account identifier is encrypted into a non-readable string of a same length as an original data plus delimiters.

6. The computer-based method of claim 4, wherein the system-supplied unique user account identifier is encrypted into a non-readable string, each character thereof is transformed into its equivalent byte representation.

7. The computer-based method of claim 1, wherein the person data satisfies the minimum data requirement if the person data includes last name, first name, middle name, date of birth, birthplace, eye color, and either a government ID or social security number.

8. The computer-based method of claim 1, further comprising retrieving and displaying person data if a unique person identifier is received, and setting a first flag to indicate either a shared entity or non-shared entity.

9. The computer-based method of claim 1, wherein the search criteria comprises at least one of person identifying information or demographic information.

10. The computer-based method of claim 1, further comprising: retrieving and displaying person data, if at least one match to the person is found in the address book; and displaying a blank form and setting a second flag to indicate a new entity, if no match to the person is found in the address book.

11. The computer-based method of claim 10, wherein retrieving and displaying person data includes setting a first flag to indicate either a shared entity or a non-shared entity.

12. The computer-based method of claim 1, wherein determining whether there is a shared entity that represents the person comprises checking a flag first.

13. The computer-based method of claim 1, wherein non-shared entity-shared entity reconciliation comprises: determining whether a shared close match is found; if no shared close match is found, defining a shared entity to represent the person in the address book if the person is a new entity, and transforming a non-shared entity into a shared entity if the person is not a new entity; and if a shared close match is found, updating a shared entity if the person is a new entity, and transferring data from a non-shared entity to a shared entity if the person is not a new entity.

14. The computer-based method of claim 13, wherein determining whether a shared close match is found comprises searching for close matches using at least one of last name, first name, middle name, mother s maiden name, sex at birth, maiden name, result of multiple birth, identical sibling, birth order, date of birth, city of birth, state/region of birth, country of birth, eye color, blood type, race, left hand span, head circumference, father's first name, nearest aged sibling's first name or dominant writing hand.

15. The computer-based method of claim 1, further comprising: if the minimum data requirement is not satisfied, based on user input, determining whether to override the minimum data requirement; and adding the person to the address book as a non-shared entity, if the minimum data requirement is overridden.

16. The computer-based method of claim 1, further comprising updating a shared entity record if it is determined that there is a shared entity that represents the person.

17. A computer readable medium tangibly embodying program instructions for implementing the method claimed in claim 1 when executed in a digital processing device.

18. The computer-based method of claim 1, further comprising searching the address book for shared close matches if it is determined that no shared entity represents the person.

19. The computer-based method of claim 18, further comprising: defining a shared entity to represent the person in the address book if no shared dose match is found and the person is a new entity; and transforming a non-shared entity into a shared entity if no shared close match is found and the person is not a new entity.

20. The computer-based method of claim 19, wherein transforming a non-shared entity into a shared entity comprises updating the first flag.

21. The computer-based method of claim 18, wherein searching the address book for shared close matches comprises: performing a close match search, obtaining a result set; displaying the result set; and if the result entry is not last result, looking up a user-selected result entry and determining whether the result entry is a match to the person.

22. The computer-based method of claim 21, wherein the close match search is performed based on at least one of person identifying information or demographic information.

23. The computer-based method of claim 22, wherein person identifying information comprises at least one of person last name, first name, middle name, date of birth, place of birth, eye color, and at least one of a government identification or social security number.

24. The computer-based method of claim 22, further comprising searching aliases if the result entry is last result and is not a match on name.

25. The computer-based method of claim 22, further comprising: defining a shared entity to represent the person in the address book if the person is a new entity; and transferring data associated with the non-shared entity to the shared entity in the address book if the person is not a new entity.

26. A computer system for defining a patient in a shared database as a unique entity to comply with HIPAA requirements to ensure confidentiality of the health information, the computer system comprising:

a first database including an address book and at least one of patient identifying information or demographic information;

a second database including clinical data;

an instructable data processor for communicating with the first and second databases;

an application service in data communication with the instructable data processor; and at least one Internet access device in data communication with the instructable data processor;

wherein the application service searches an address book for a match to the person using a search criteria input by a user and if no match to the person is found, receives person data input by the user and determines whether the person data satisfies a minimum data requirement, where the person data is representative of the person, and if it is determined that the minimum data requirement is not satisfied, it generates a non-shared entity to represent the person in the address book, and if it is determined that the minimum data requirement is satisfied, determines whether there is a shared entity that represents the person, and if it is determined that no shared entity represents the person, based on an outcome of a non-shared entity-shared entity reconciliation, it performs one of generating a shared entity to represent the person in the address book, transforming a non-shared entity into a shared entity, or transferring data from a non-shared entity to a shared entity, wherein the shared-entity grants access to data associated with the shared-entity and the non-shared entity prevents access to data associated with the shared entity.

27. The computer system of claim 26, wherein the address book maintains information on all entities in the system, and wherein all entities in the system are identified as either a shared entity or a non-shared entity.

28. The computer system of claim 26, wherein the Internet access device comprises at least one of a workstation, PDA, laptop computer, notebook computer, or a Microsoft Windows-enabled mobile device.

29. The computer system of claim 26, wherein the first database is designed to be run either integrated with the second database or hosted as a separate database system in a geographically different site from the second database.

30. The computer system of claim 26, wherein transforming a non-shared entity into a shared entity comprises updating a first flag.

* * * * *